United States Patent [19]
Desjonqueres

[11] Patent Number: 6,001,378
[45] Date of Patent: Dec. 14, 1999

[54] COMBINATIONS OF PEROXIDE LIPIDS AND ORGANOSILICON COMPOUNDS, COSMETIC AND DERMATOLOGICAL COMPOSITIONS CONTAINING SAME, AND USES THEREOF, IN PARTICULAR FOR TREATING ALOPECIA

[75] Inventor: Stéphane Desjonqueres, Maisons-Laffitte, France

[73] Assignee: Laboratoires Carilene, Montesseon Cedex, France

[21] Appl. No.: 09/117,039

[22] PCT Filed: Jan. 24, 1997

[86] PCT No.: PCT/FR97/00141

§ 371 Date: Jul. 24, 1998

§ 102(e) Date: Jul. 24, 1998

[87] PCT Pub. No.: WO97/26892

PCT Pub. Date: Jul. 31, 1997

[30] Foreign Application Priority Data

Jan. 26, 1996 [FR] France .................................. 96 00922

[51] Int. Cl.$^6$ ...................................................... A61K 7/06

[52] U.S. Cl. ...................... 424/401; 424/450; 424/78.37; 514/63; 514/552; 514/880

[58] Field of Search .................................... 424/401, 450, 424/78.37; 514/63, 880, 552

[56] References Cited

U.S. PATENT DOCUMENTS 5,254,585 10/1993 Desjonqueres .......................... 514/552

*Primary Examiner*—Jose' G. Dees
*Assistant Examiner*—Michael A. Williamson
*Attorney, Agent, or Firm*—Dennison, Meserole, Scheiner & Schultz

[57] ABSTRACT

Combinations, in particular for use as the active principle in a cosmetic or pharmaceutical and particularly dermatological composition, containing 1–6 parts by weight of peroxidised lipids per 0.01–0.1 parts by weight, based on the organic silicon, of a biologically active organosilicon derivative, are disclosed. Cosmetic or dermatological compositions containing such combinations are also disclosed. Said compositions are particularly useful for treating alopecia.

11 Claims, No Drawings

COMBINATIONS OF PEROXIDE LIPIDS AND ORGANOSILICON COMPOUNDS, COSMETIC AND DERMATOLOGICAL COMPOSITIONS CONTAINING SAME, AND USES THEREOF, IN PARTICULAR FOR TREATING ALOPECIA

The present invention relates to novel combinations of peroxidised lipids and organosilicon compounds, cosmetic and dermatological compositions containing them, as well as to their applications, especially for the treatment of alopecia.

Hair loss, also known as alopecia, is a problem which is most particularly spread over the whole of the population, especially in the male population but also in the female population.

Many studies have been dedicated to this problem. As regards female alopeciae disseminatae, the development on female alopeciae disseminatae, carried out by P. Reygagne, and which appear in bedc, 1993, 1, 7, 327–338, may be cited in particular. In this study, it emerges that alopeciae disseminatae are currently the subject of three types of treatment:

general treatments, such as the combination of vitamin B5 and vitamin H or vitamin B8, minoxidil prescribed locally which causes a moderate re-growth in 30% of cases, but the positive effect of which ceases to manifest itself in the 3 to 6 months following the stopping of the applications, endocrinological treatments in cases of androgenetic alopeciae.

In general, androgenetic alopecia is the most frequent of alopeciae and, without doubt, that for which the therapeutic demand is the highest. However, the anti-androgenetic treatments per os which have a certain effectiveness in the woman are not practical in the man and no local anti-androgenetic treatment has found long-lasting effectiveness. The only local treatment being able to demonstrate in several controlled studies a certain effectiveness in the man is minoxidil in a twice-weekly local application. The first studies made between 1982 and 1986 were relatively optimistic with 18 to 53% re-growth. Such a study is given in: Androgenic alopecia: clinical aspects and treatment, in "Hair and Hair Diseases" C. E. ORPHANOS, R HAPPLE (Eds), Springer-Verlag, Berlin Heidelberg 1990, PP 485–527. Cosmetically acceptable re-growths are in fact rare, as related by RUSHTON D. H., VUGER W. P., COTTERIL P. C., KINGSLEY P., JAMES K. C. in "Quantitative assessment of 2% topical Minoxidil in the treatment of male pattern baldness", Clin Exp Dermatol, 1989, 14, 40–6. Moreover, OLSEN E. A., WEINER M. S. AMARA I. A., DELONG E. R., have indicated in the article entitled "Five-year follow-up of men with androgenetic alopecia treated with topical Minoxidil" in J. Am Acad Dermatol 1990, 22, 643–6, a slow return of the hair loss after 1 year of treatment, even if the treatment is continued. Furthermore, a systemic diffusion limits the increase in the local concentration of minoxidil and the preparations currently marketed are all dosed at 2% minoxidil.

Various peroxidised lipids are known, which are notably obtained by a peroxidation of natural vegetable oil. The following patents shall be cited in particular: BSM N°2 330 M, EP-A-293 535, FR-A-2 591 112, EP-A-225 831, EP-A-225 832, EP-A-225 833, EP-A-226 506, FR-A-2 461 744, FR-A-2 539 142 and EP-A-117 962, which relate either to the preparation of such peroxidised lipids, or to their applications in various fields, particularly in the treatment of certain illnesses in the field of rheumatology or traumatology, or even as a healing product.

Peroxidised lipids of this type have also been used according to European patent EP-A-0 480 983 for the treatment of circulatory insufficiencies by local application.

Many references are found in the literature which relate to the activity of organic silicon on the stimulation of the biosynthesis of collagen or of elastin, in the reconstitution of the damaged connective tissue. It emerges from the experimental works given in the various publications, that in particular, the organic silicon causes a return to a normal level of the arterial wall degraded by the attack of an artificially caused atheroma.

More specifically, in J. Med. Esth and Chir. Derm., volume XII, 47, September 1985, pages 187–190, F. MARCHI-LIPSKI and F. DANIEL have carried out a bibliographical analysis concerning the therapeutic interest of silicon in the ageing of connective tissue. It emerges from this study that silicon has a most particular importance in the upkeep of the integrity of connective tissue and that the organosilicon derivatives enable efficiently fighting against the ageing of connective tissue in all its forms.

It also emerges from this article that there exists soluble organic silicon derivatives which can be used according to various administration routes and notably by local application.

Amongst the many therapeutic applications cited in this article, the application for improving the growth and the density of the hair is raised.

In the chapter dedicated to the biological activity of silatranes in Topics in Current Chemistry, vol. 84, pages 77–135, 1979, Michail G. Voronkov has demonstrated the importance of these silatranes in the treatment of alopecia.

Furthermore, the French patent FR-2,645,863 described silicon compounds in the form of molecular complexes of a silanol which are prepared by the reaction of an alkaline salt or ammonium salt of a silanol with an acid in the presence of a zeolite. These silanol complexes may, inter alia, be used for improving the re-growth of hair.

It is this type of complex which is used for the preparation of the product sold under the commercial trade name M 44 by Laboratoires CARILENE.

Such a product for stopping hair loss acts, due to the presence of organic silicon, as:

a tonic for the vascular walls, which leads to the improvement of the papillary vascularization, a regulator of cell metabolism which favours the anagenic phase of the pilary cycle, a stimulant of the synthesis of collagen and of elastin which enables the restructuration of the pilary stem, a sebo-regulator, which leads to the decrease in the excess of sebum.

Pursuing his research with the view to improving the performances of the products for treating alopecia, the inventor of the present invention has noticed that combinations of peroxidised lipids and organic silicon derivatives, in particular silanol derivatives led to a considerable increase in the activities of the two products, enabling perfectly unexpected performances in the treatment of alopecia, in particular alopecia of the androgenetic type.

These combinations do in fact allow obtaining results at least equivalent to those obtained with minoxidil as well as preventing the drawbacks of the latter product, namely the lack of remanance of the observed effect once the treatment is stopped. Furthermore, another non-negligible advantage of these combinations with the respect to minoxidil is that they cause no increase in seborrhoea during treatment and necessitate only one application per day and not two.

A randomised controlled study of the effectiveness of these combinations has enabled demonstrating, without ambiguity, the effectiveness of these combinations. The effectiveness of these combinations was compared to that of minoxidil, the only current reference product in the treatment of androgenetic alopecia. The experimental method for making this comparison was that of phototrichograms, the only method recognised today as being perfectly reliable. The protocol and the results of this study are given in the examples of the present text.

Hence, according to a first aspect, the invention relates, as novel industrial product, to combinations of the two types of chemical products, namely peroxidised oils and organic silicon compounds, in particular silanol derivatives.

According to a second aspect, the invention also relates to cosmetic compositions as well as to pharmaceutical compositions, notably dermatological compositions, which contain these combinations as active principle.

According to another of its essential aspects, the invention also relates to the use of these combinations and compositions in the treatment of alopecia.

According to another aspect, the invention relates to other applications of these combinations and compositions in which the same effect of potentiation of the effect of one of the two active substances by the other has been observed. In particular, this is what is observed for the treatment of the effects of ageing of the skin, healing and tissue regeneration, as well as in the treatment of cellulite.

More specifically, according to one of its essential characteristics, the invention relates to a combination, notably useful as the active principle in a cosmetic or pharmaceutical composition, notably dermatological composition, characterised in that it contains 1 to 6 parts by weight of peroxidised lipids per 0.01 to 0.1 part by weight based on the organic silicon of a biologically active organosilicon compound.

According to a particularly advantageous embodiment, these combinations are in the form of stable emulsions.

The peroxidised lipids, which can be used in accordance with the invention, may be of very varied chemical nature but advantageously have a peroxidation rate between 30 and 500 milli-equivalents per kilo, preferably between 50 and 300 milli-equivalents per kilo, preferably still between 50 and 150 milli-equivalents per kilo.

According to a particular embodiment, these lipids advantageously have a glyceride oxides content between 5 and 40%.

In accordance with the invention, at least one peroxide obtained by peroxidation of lipids of plant origin, for example in the form of at least one natural vegetable oil, is preferably used as peroxidised lipids. Preferably, these oils are selected from sweet almond oil, hazelnut oil, peanut oil, maize oil, grape seed oil, sesame oil and oil of safflower.

According to a particular embodiment of the invention, peroxidised lipids are used, which are principally or mainly constituted of triglycerides of the general formula:

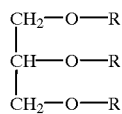

in which the radicals R are mainly represented by the peroxidised octadecanoic and octdecanoic acids.

The biologically active organosilicon derivatives, which are useful according to the invention, can be any water-soluble organic silicon derivative and which is known for its biological activity.

These may be free or condensed soluble organosilanol, organosilanediol or organosilanetriol derivatives. These soluble derivatives are advantageously in the form of salts or complexes of the corresponding organosilanols, referred to hereinafter as silanol as a means of simplification.

These derivatives will advantageously be selected from soluble organosilanol derivatives of formula $[R_n Si(OH)_{4-n}]$ x, in which $0 < x \leqq 4$, the n groups R are identical or different and represent independently hydrogen or an alkyl or aralkyl group and n is between 1 and 3.

The nature of the various R groups is such that said organosilanols correspond to soluble and non-toxic derivatives.

As examples of such soluble silanols derivatives, the following may be cited: potassium monomethylsilanetriol, perhydrolysed dimethylsilisalycilate, monomethylsilanetriol mannuronate, dimethylsilanol hyaluronate, ascorbyl methylsilanol pectinate, methylsilanol aspartate hydroxyprolinate.

In general, any organosilanol which is soluble in water, and therefore biologically active and assimilated, can be used as silanol derivative.

As other examples of silanol derivatives which can be used to prepare the combinations useful according to the invention, silicon compounds can also be cited, which are described in the French patent FR-2,645,863 given here by reference. More specifically, these silicon compounds are in the form of a molecular complex of a silanol of general formula

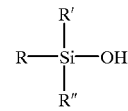

wherein R is an alkyl or aryl group and R' and R" are alkyl, aryl or OH groups, and an alkaline or ammonium derivative of an acid.

Such products are obtained in particular from an alkaline salt or an ammonium salt of a silanol, which is combined with an acid in the presence of a zeolite which allows complete reaction of the two products.

As emerges clearly from the following examples, the interest of the combinations according to the invention is that they can be used as active principle in cosmetic or pharmaceutical compositions, notably dermatological compositions, by conferring to these compositions not only the combined advantages of the two types of active principles of which they are comprised, but also a true synergy of these activities.

This synergy proves to be particularly interesting in the case of the treatment of alopecia, in particular androgenetic alopecia.

The combinations of the invention enable, due to the presence of oxidised glycerol triesters, to act upon the almost immediate re-establishment of the arterial blood flow within the pilary follicle, consequently, to cause a rush of blood which can rapidly act upon the stopping of an excessive hair loss, and can even eventually permit the re-growth of the vellus.

Concurrently to this action, the soluble organic silicon contained in the combination intervenes both to vehicle the first active principle and to render the damaged arteries of the follicle their motor function, which assures an upkeep in the long term of the normal blood flow, even after the stopping of the treatment, by the virtue of the regeneration of the arterial connective tissue.

Thus, a synergy of the two therapeutic activities is created which is linked to the action of blood flow accelerator and to the healing action by activation of the cellular renewal due to the presence of oxidised glycerol triesters, and to the action of catalyst of the biosynthesis of the connective tissue due to the presence of the silicon derivative, which lead to the restructuration of the walls of veins, arteries and capillaries.

The two active principles which constitute the combinations of the invention have therefore a conjugated action, which leads to a greater irrigation in the pilary follicle at the same time as to a regeneration of hair-nourishing system.

Hence, according to one of its essential aspects, the present invention relates to cosmetic or pharmaceutical compositions, notably dermatological compositions, which contain as active principle a combination as described above.

These compositions advantageously contain from 1 to 6% by weight of peroxidised lipids and from 0.01 to 0.1% by weight, based on the organic silicon, of a biologically active organosilicon derivative, in particular a soluble silanol derivative, and a cosmetically or pharmaceutically acceptable vehicle.

These compositions can be used in any field in which a potentiation of the activity of the peroxidised lipids by that of the silicon derivatives is sought.

This effect has been particularly observed in the case of the treatment of alopecia, in particular androgenetic alopecia, as emerges from the examples.

However, the interest of the combinations is not limited to this type of treatment since they may be used in any type of cosmetic or pharmaceutical treatment, notably dermatological treatment, in which it is sought to treat or to look after the skin, the scalp or the hair, in particular with the view to fighting against the effects of ageing, for improving healing and tissue regeneration as well as for fighting against hair loss and for improving hair re-growth.

According to these methods, a cosmetically or pharmaceutically active amount of a composition such as described above is applied onto the part of the body to be treated.

Consequently, if the combinations according to the invention prove to be particularly effective for the preparation of pharmaceutical compositions, notably dermatological compositions, for application onto the scalp and/or the hair with the view of treating alopecia, notably androgenetic alopecia, the combinations also prove to be very useful in different treatments, such as the treatment of cellulite, the upkeep or the treatment of the hair with the view of fighting against its ageing, as well as any treatment for improving the healing or the regeneration of tissues.

The compositions according to the invention may be in any galenic form which can be used in function of the effect sought after and of the area of the body to be treated. These compositions may be lotions, gels, creams, shampoos, these galenic forms being intended for the scalp or the application onto the face or the body.

The following examples are given purely as an illustration of the invention.

EXAMPLES

Unless otherwise indicated, the concentrations in the Examples below are given in percentages by weight.

Example 1

| Formula of a cream for care of the body or the face. | | |
| --- | --- | --- |
| Oxidised glycerol triesters | | 10 |
| Potassium monomethylsilanetriol | | 0.5 |
| Excipients, preservatives, perfumes | qs | 100 |

This cream is applied by light massage once or twice a day in a treatment of 3 months minimum.

This cream is particularly useful for improving the cell renewal, for fighting against cellulite and stretch marks. Furthermore, it improves healing and acts as an anti-inflammatory and has an analgesic and soothing effect.

Example 2

| Formula of a lotion for care of the body or the face | | |
| --- | --- | --- |
| Oxidised glycerol triesters | | 3 |
| Potassium monomethylsilanetriol | | 0.1 |
| Cosmetic alcohol 99° | | 15 |
| Permutated water, perfumes, preservatives, | qs | 100 |

This lotion is applied with the aid of cotton wool at the rate of a few drops of lotion, in the evening, on the body or the face. The application is renewed for a minimum of 3 months.

This lotion is particularly useful for improving cell renewal, for fighting against cellulite and stretch marks. Furthermore, it improves the healing and acts as an anti-inflammatory and has an analgesic and soothing effect.

Example 3

| Hair lotion | | |
| --- | --- | --- |
| A composition having the composition below, in percentages by weight, is prepared: | | |
| Potassium monomethylsilanetriol citrate | | 1 |
| Protein hydrolysate | | 0.5 |
| Keratin hydrolysate | | 0.5 |
| Amino acid complex | | 0.1 |
| Peroxidised maize oil (Epaline 100 ®) | | 3 |
| Absolute alcohol for cosmetology | | 10 |
| Gardienia essence | | 0.05 |
| Excipient, preservative and demineralised water | qs | 100 |

This lotion is applied onto the scalp, part by part, at the rate of a few drops, preferably in the evening. The application is renewed for 3 months minimum.

Example 4

Clinical test of effectiveness against alopecia.

The effectiveness of the composition of Example 3 against hair loss and seborrhoea was tested, in comparison with minoxidil on a population of 60 men of 18 to 65 years old suffering full androgenetic alopecia, having an alopecia of the androgenetic type at stage III to VI according to the Hamilton classification.

The comparative test was carried out under the following conditions over a period of 9 months. The patients were grouped into two homogeneous groups of the same importance.

a) Protocol of the test a-1: Initial evaluation

Each patient was subjected to an initial assessment (at D0) which comprises:

1—Measuring of the diameter of the area of alopecia on the top of the head.

2—Filling-in a questionnaire.

3—Carrying out a pre-therapeutic phototrichogram:

This necessitates in the first instance the shaving and the semi-permanent tattooing of the area to be photographed. This tattoo is done with the aid of disposable sterile needles having three branches. The area is selected in front of the vertex in an alopecic area having a percentage of telogenic hair which is a priori greater than 20%. On a surface of about 2 cm$^2$, the hair is cut short on D0 with the aid of curved scissors. Two semi-permanent tattoo points then allow marking out an imaginary square of 7×7 mm within which the hairs will be counted. These two tattoo points will correspond to two fixed marks on the viewing system. It is necessary to be aware that the hair will all have the same parallel orientation in the interior of the imaginary square of 7×7 mm.

After this operation, a macrophotograph is taken on D0 under standardised and perfectly reproducible conditions of distance, lighting and enlargement (×3). A second comparative photograph is taken on D0+2 days. The comparison of the two photographs enables differentiating the hairs in anagenic phase which have grown, and hairs in telogenic phase, which have not grown.

This technique therefore enables studying the density of hairs per cm$^2$, the number of anagenic hairs (A), the number of telogenic hairs (T), the ratio A/T, the percentage of anagenic hairs (A %), the speed of hair growth, their diameter (D).

The phototrichogram is repeated after three months from the first period of treatment ($M_3$), a third time three months later, upon the completion of the second period of treatment ($M_6$).

4—Sampling of the hair

A bunch of hair is taken from the area to be shaven for the phototrichogram. This bunch shall be linked to the base, stored in a numbered tube, and allows measuring of the diameters of the hair later on.

a-2. Treatment

After taking the first phototrichogram, each patient is given a box containing the three first months of treatment (13 weeks). These boxes are numbered from 1 to 60, and the numbers are attributed to each patient according to the order of his arrival in the study. Each box contains either three flasks of minoxidil, or three flasks of lotion of example 3. Each flask of minoxidil and each flask of lotion according to the invention has on it a sticky label bearing the number of the box to which it belongs.

The test being randomised, the numbers of the boxes (30 boxes of minoxidil and 30 boxes of lotion of example 3) are attributed by virtue of a randomisable table which is equilibrated every four patients. During the period of treatment of 13 weeks, each patient uses either 1 ml of minoxidil applied locally every day, morning and evening, or 3 ml of lotion of example 3 applied locally once a day in the evening.

At the end of the first period of treatment (noted time M3), after the second monitoring visit and the preparation of this second phototrichogram, a second numbered box of treatment was given to each patient. This box contains either the product of example 3, or minoxidil. The second period of treatment lasts also for three months (13 weeks). At the end of this period (noted time M6), a third phototrichogram is made. Finally, a fourth phototrichogram was made on the different patients after the complete stopping of the treatment for 13 weeks (noted time M9).

During these treatments, the following treatments are authorised:

shampoos: free. The patients may wash their hair every day if they wish, with the shampoo of their choice. The best is that they pursue their normal shampooing if this is convenient to them.

Colouring, bleaching and perms: these are authorised. It is simply necessary to avoid that they are not done during the period of the preparation of phototrichograms.

In contrast, the following are not authorised:

Any local or general treatment which may have an effect upon the growth or of the loss of the hair is forbidden throughout the study, and during the three months preceding the inclusion. Particularly forbidden are: prostaglandins, rubefacients, any vasodilator, any anti-androgen, and any local hormonal treatments.

b) Results

The study showed, for the anagenic hair counts, telogenic hair counts, and total hair counts, as well as the anagenic/telogenic ratios of the months $M_0$ and $M_6$, an equivalence between the two products since the very slight differences that may be noticed, of which certain are in favour of the product of example 3, are not statistically significant.

The clinical projection of these counts leads the clinician to conclude a real anti-hair loss activity of the two products as well as a certain activity upon the re-growth.

The statistical study led from the results of the phototrichograms leads concluding the equivalence between the two products tested as regards the anagenic (A) over telogenic (T) ratios. These results are clearly given in table 1 below:

TABLE 1

Evolution of the ratio between M6 and M0

| | | Treatment group | | |
| --- | --- | --- | --- | --- |
| | | Lotion of example 3 | Minoxidil | Total |
| Difference M6/M0:A/T | N | 32.00 | 28.00 | 60.00 |
| | Missing data | 1.00 | 0.00 | 1.00 |
| | Average | 0.0 | −0.5 | −0.2 |
| | Standard deviation | 2.3 | 2.9 | 2.6 |
| | Minimum | −4.75 | −9.13 | −9.13 |
| | Maximum | 7.33 | 6.14 | 7.33 | wherein it appears that no difference was detected between the two treatment groups as regards the evolution of the ratio of the number of anagenic hairs over the number of telogenic hairs between M6 and M0.

Furthermore, no significant difference was detected for this same evolution between M3 and M0 (p=0.057).

Furthermore, table 2 below shows that no difference was observed for the two products as regards the difference in the percentages of anagenic hairs between M6 and M0.

TABLE 2

Percentage of anagenic hair:-difference M6–M0

|  |  | Treatment group | | |
|---|---|---|---|---|
|  |  | Lotion of example 3 | Minoxidil | Total |
| Difference M6/M0:% Anagenics | N | 32.00 | 28.00 | 60.00 |
|  | Missing data | 1.00 | 0.00 | 1.00 |
|  | Average | −0.4 | −3.2 | −1.7 |
|  | Standard deviation | 11.0 | 12.8 | 11.9 |
|  | Minimum | −32.54 | −39.80 | −39.80 |
|  | Maximum | 23.66 | 22.40 | 23.66 |

Furthermore, no difference was detected between the two groups of treatment between M3 and M0.

In contrast however, the table 3 below shows that the total number of hairs in the marks depends upon the treatment followed.

TABLE 3

Total number of the hair in the marks-difference M6–0

|  |  | Treatment group | | |
|---|---|---|---|---|
|  |  | Lotion of example 3 | Minoxidil | Total |
| Difference M6/M0:Total | N | 32.00 | 28.00 | 60.00 |
|  | Missing data | 1.00 | 0.00 | 1.00 |
|  | Average | −2.9 | 6.4 | 1.4 |
|  | Standard deviation | 9.4 | 9.4 | 10.5 |
|  | Minimum | −22.00 | −18.00 | −22.00 |
|  | Maximum | 22.00 | 28.00 | 28.00 |

A significant difference ($p<0.001$) was detected between the two groups of treatment as regards the evolution of the total number of the hairs in the marks between M6 and M0.

As an indication, there was also a significant difference ($p=0.001$) between M3 and M0. This difference may be explained by the increase of the number of telogenic hairs in the minoxidil group. It is to be noted that this type of hair (telogenic) is led to fall in the three months.

A very clear difference is also observed as regards the number of telogenic hairs after 6 months of treatment. This difference is clearly seen in table 4 below.

TABLE 4

Number of telogenic hairs-difference M6–M0

|  |  | Treatment group | | |
|---|---|---|---|---|
|  |  | Lotion of example 3 | Minoxidil | Total |
| Difference M6/M0:T | N | 32.00 | 28.00 | 60.00 |
|  | Missing data | 1.00 | 0.00 | 1.00 |
|  | Average | −0.8 | 3.4 | 1.2 |
|  | Standard deviation | 6.2 | 8.1 | 7.4 |
|  | Minimum | −16.00 | −12.00 | −16.00 |
|  | Maximum | 10.00 | 29.00 | 29.00 |

A significant difference ($p=0.025$) was detected between the two groups of treatment as regards the evolution of the number of telogenic hairs between M6 and M0.

As an indication, there was no difference for this evolution between M3 and M0.

From the results of this statistical study given in the tables above, it nevertheless emerges a better quality of hair after treatment for 6 months with the lotion of the invention with the respect of that observed after treatment with minoxidil since, even if minoxidil further favours the re-growth of the hair, the telogenic hairs are found in a higher percentage.

From a clinical point of view, the important improvement brought about by the product of example 3, in comparison with minoxidil, must be taken into account:

One sole application per day (instead of 2)

A non-greasy product, which did not necessitate shampooing after use,

Absence of seborrhoea (minoxidil stimulates the production of sebum by the sebaccic glands)

A hair whose diameter has increased with respect to the minoxidil group

An overall approach of the results to M6 has led the clinician to indicate a long term action, which must permit the stopping of the treatment once good results are obtained, whereas minoxidil necessitates a life-time treatment, since the upkeep of the results obtained is linked to an uninterrupted use. This "slow-release" treatment was confirmed by results at M9

A low percentage of alcohol.

The results of this comparative study over 9 months indicate in table 5 below as regards the reference product minoxidil for a twice-weekly application of the product during the first six months of the study, and in table 6 below for the product of example 3, applied once daily, during the first six months of the treatment, the treatments being stopped in both cases after six months.

TABLE 5

|  | Reference product | | | |
|---|---|---|---|---|
|  | M0 | M3 | M6 | M9 |
| A | 45.89 | 59.33 | 49.43 | 42.71 |
| T | 14.29 | 11.83 | 17.57 | 19.10 |
| A/T | 3.21 | 5.01 | 2.82 | 2.23 |
| A% | 76.55 | 83.93 | 74.03 | 69.49 |
| N* | 61.40 | 70.77 | 67.00 | 61.81 |
| D ($\mu$m) | 70.00 | 73.71 | 77.18 | 77.76 |

N*:Number of hairs in the marks

TABLE 6

|  | Product of example 3 | | | |
|---|---|---|---|---|
|  | M0 | M3 | M6 | M9 |
| A | 47.24 | 51.45 | 46.73 | 44.65 |
| T | 15.64 | 12.21 | 13.23 | 15.96 |
| A/T | 3.02 | 4.21 | 3.53 | 2.79 |
| A% | 75.07 | 80.59 | 76.68 | 73.61 |
| N* | 62.68 | 63.67 | 60.27 | 60.92 |
| D ($\mu$m) | 74.85 | 79.68 | 80.31 | 80.27 |

The experimental protocol of the comparative clinical study with minoxidil allows prolonging the study for three months after the stopping of the treatment.

The growth parameters-anagenics, percentage of anagenics, number of total hair-remain with a remarkable stability in the group treated by the product of example 3, against a rapid return to the pathology in the group treated by minoxidil.

Consequently, the therapeutic regimen recommended with the product of example 3 consists in taking advantage of this "slow-release" effect and in stipulating periods of stopping of treatment of three months, after the first three months of initial treatment. A treatment of three months will therefore be envisaged, followed by three months of stopping of the treatment, and then a continuation of the treatment for three months, etc.

This obviously represents an important advantage for the use of the product in that it is quality of life or the price of treatment.

What is claimed is:

1. A combination comprising 1 to 6 parts by weight of peroxidized lipids and 0.01 to 0.1 part by weight based on organic silicon of a biologically active organosilicon compound.

2. The combination according to claim 1, in the form of a stable emulsion.

3. The combination according to claim 1, wherein said peroxidized lipids have a peroxidation rate between 30 and 500 milliequivalents per kilo.

4. The combination according to claim 1, wherein said peroxidized lipids are obtained by peroxidation of lipids of plant origin.

5. The combination according to claim 4, wherein the lipids of plant origin are obtained from at least one natural vegetable oil selected from the group consisting of sweet almond oil, hazelnut oil, peanut oil, maize oil, grape seed oil, sesame oil and oil of safflower.

6. The combination according to claim 1, wherein the peroxidized lipids have a glyceride oxides content between 5 and 40%.

7. The combination according to claim 1, wherein said organosilicon compound is a water-soluble organosilanol, organosilanediol or organosilanetriol derivative.

8. The combination according to claim 7, wherein said water-soluble derivative is a silanol derivative of formula $[R_n Si(OH)_{4-n}]x$, in which $0 < x \leq 4$, the n groups R are identical or different and represent independently hydrogen or an alkyl or aralkyl group and n is between 1 and 3.

9. A cosmetic or pharmaceutical composition containing as active principle a combination according to claim 1.

10. The composition according to claim 9, containing from 1 to 6% by of peroxidised lipids and from 0.01 to 0.1% by weight, based on the organic silicon, of a biologically active organosilicon derivative and a cosmetically or pharmaceutically acceptable vehicle.

11. A method of treatment of the skin, the scalp or the hair, for fighting against the effects of ageing, for improving healing and tissue regeneration, for fighting against hair loss, improving hair re-growth or treating alopecia, comprising applying onto the skin, scalp or hair an effective amount of a composition according to claim 9.

* * * * *